United States Patent [19]
Bruzzese et al.

[11] 3,961,047
[45] June 1, 1976

[54] ESTERS OF PARTRICIN DERIVATIVES

[75] Inventors: Tiberio Bruzzese; Giuseppe Ghielmetti, both of Milan, Italy

[73] Assignee: SPA-Societa Prodotti Antibiotici S.p.A., Italy

[22] Filed: Feb. 13, 1974

[21] Appl. No.: 441,988

[30] Foreign Application Priority Data
Feb. 15, 1973 United Kingdom............... 7488/73

[52] U.S. Cl................................ 424/122; 424/121
[51] Int. Cl.² ........................................ A61K 35/74
[58] Field of Search ........................... 424/115–122

[56] References Cited
OTHER PUBLICATIONS

*Chemical Abstracts* 77: 14812t (1972).
*Chemical Abstracts* 78: 67526e (1973).
*Chemical Abstracts* 79: 74168p (1973).

*Primary Examiner*—Sam Rosen
*Attorney, Agent, or Firm*—Wenderoth, Lind & Ponack

[57] ABSTRACT

The present invention provides new esters of partricin and of N-substituted derivatives of partricin.

3 Claims, 4 Drawing Figures

1

ESTERS OF PARTRICIN DERIVATIVES

BACKGROUND OF THE INVENTION

There is an ever increasing need for new and active materials which are effective against micro-organisms, such as fungi and protozoa, and which are more effective than and/or less toxic than hitherto known materials.

In U.S. Pat. No. 3,773,925, there is described the new amphoteric antibiotic partricin and in U.S. Pat. No. 3,780,173, there is described the methyl ester of partricin.

Although partricin and its methyl ester are both valuable compounds, there is still a need to improve them by rendering them less toxic and/or by making them more effective.

It is, therefore, an object of the present invention to provide new and highly effective derivatives of partricin.

SUMMARY OF THE INVENTION

Thus, according to the present invention, there are provided the alkyl esters of partricin and of N-substituted derivatives of partricin, the alkyl radical of which contains at least 2 carbon atoms and preferably contains 2 to 6 carbon atoms, in the case of partricin esters and the alkyl radical of which preferably contains up to 6 carbon atoms, in the case of N-substituted derivatives of partricin.

DETAILED DESCRIPTION OF THE INVENTION

Figure 1:
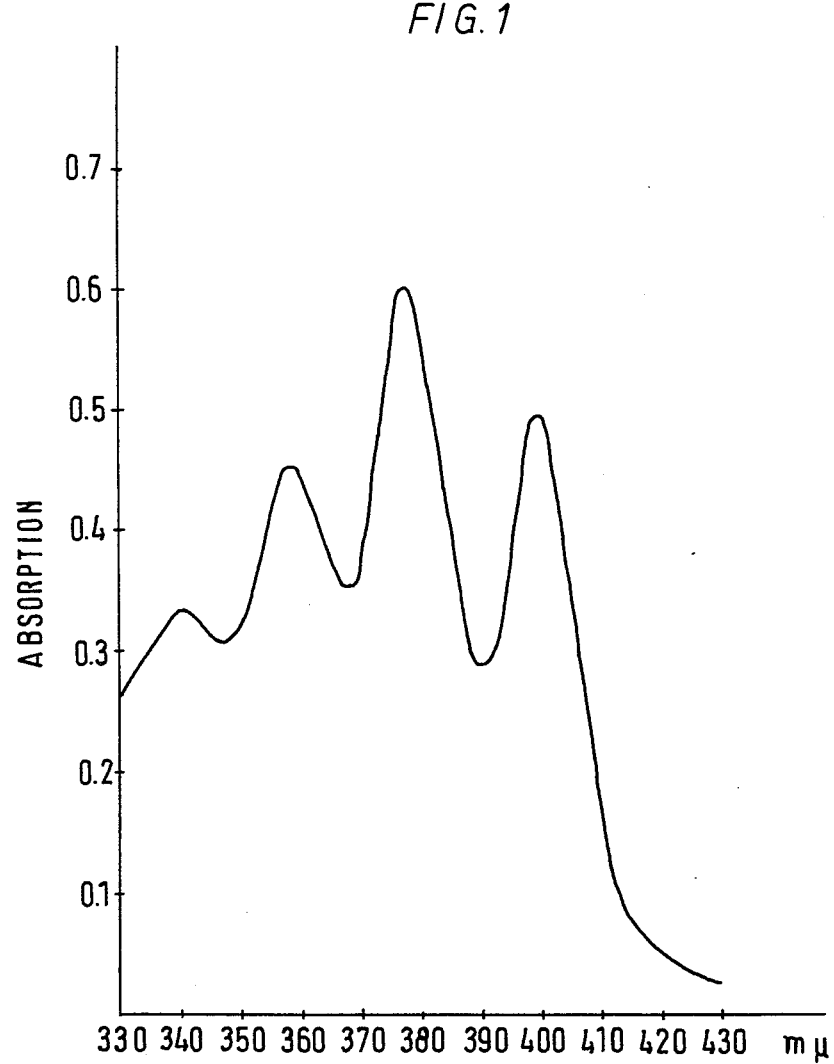

The new esters of the present invention have valuable biological activities and, in particular, are highly active against numerous species of fungi, yeasts and protozoa.

An important property of the new esters of the present invention is the fact that, whereas they very often have the same or, in some cases, even better biological activity than the starting materials, i.e. partricin and its N-derivatives, they are generally less toxic and less haemolytic, which means that the new esters are of considerable therapeutic interest. The non-esterified N-derivatives have, when compared with partricin, a marked, even if more reduced, antifungal and antiprotozoal activity and a lower toxicity.

Partricin is an antibiotic substance with a polyene macrolidic structure produced by the metabolism of a particular strain of *Streptomyces aureofaciens* (NRRL 3878). It is a yellow crystalline powder, which is easily identifiable by its physico-chemical properties, by elemental analysis and analysis of the functional groups, by thin layer chromatography and by infra-red and nuclear magnetic resonance spectra; in particular, the ultra-violet spectrum, which, in ethanolic solution shows absorption maxima at 401, 379, 359 and 341 m$\mu$, indicates a heptaenic structure in accordance with other examples in the literature. The presence, among the other substituents, of a free carboxyl and of two nitrogen-containing groups, gives the substance amphoteric properties and makes it ideal for various reactions on both the functional groups.

From a biological viewpoint, partricin is active against numerous fungi, such as *Candida albicans* (Minimum Inhibitory Concentration (MIC) about 0.3 – 0.6 mcg./ml.) and against certain protozoa, such as *Trichomonas vaginalis* (MIC about 0.15–0.20 mcg./ml.). Despite its high biological activity and the relatively good tolerance by the oral route ($DL_{50}$ about 300 mg./kg. in mice), the possibility of a practical utilisation of partricin is severely limited due to its high toxicity when administered intraperitoneally ($LD_{50}$ about 0.5 mg./kg. in mice).

The new ester derivatives of partricin and of N-substituted partricin according to the present invention are also crystalline solids with a yellow to dark yellow colour which are insoluble or sparingly soluble in water and in the usual organic solvents, such as diethyl ether, benzene and the like, more soluble in alcohols and very soluble in dimethylsulphoxide, pyridine and dimethylacetamide. However, whereas the alkyl esters of partricin cannot be solubilised in an aqueous medium at about neutral pH, the esters of N-substituted partricin can be dissolved, for example, with the use of sodium hydroxide in stoichiometric quantities, when an appropriate functional group (carboxyl) is introduced with the N-substituent. Since water solubility is an important property for the practical use of the polyenic substance, it is more generally obtained by the use of certain surface-active agents, for example, sodium desoxycholate, sodium lauryl sulphate and the like, which result in the formation of colloidal solutions or pseudo-solutions of the partricin esters.

A preferred method for the preparation of the new esters according to the present invention is the reaction of partricin or partricin derivatives with appropriate diazo compounds, especially with the diazoalkanes. Diazo compounds have a marked toxicity and are potentially explosive in a concentrated state when they decompose. Therefore, they must be used with caution and are usually diluted with volatile solvents, for example with diethyl ether or tetrahydrofuran.

The polyene substance can be used in dimethylsulphoxide solution, but other inert solvents, for example pyridine, dimethylacetamide and other solvents inert to diazo compounds can be employed. The reaction is usually carried out by adding a solution of the diazo compound in slight excess to a solution of partricin or N-substituted partricin and leaving the mixture to stand for periods of time varying from 1 to 24 hours, generally for 4–8 hours. The temperature of the reaction mixture is kept between 0° and 50°C. and generally at about ambient temperature, i.e. 15°–30°C.

The desired ester can then be isolated in high yields by precipitation with an excess of an appropriate solvent, for example diethyl ether, benzene or water, followed by filtration. The crude compound thus obtained can subsequently be purified by crystallisation with appropriate mixtures of solvents, for example dimethylsulphoxide-water, dimethylacetamide-ether and the like, or by thin layer chromatography on silica gel, using more or less complex mixtures of eluents.

We have also found that it can be advantageous to add small quantities of alkaline substances to the reaction medium. In particular, ammonium hydroxide can be used in catalytic to stoichiometric quantities, as well as triethylamine; a pH of 10–10.5 (measured after dilution with water to 1%) is often optimal for reducing the formation of by-products to a minimum and in producing the highest purity and microbiological activity of the reaction products. It can sometimes also be advantageous to add a small amount of ethanol to the reaction mixture: ethanol apparently seems to be able to protect the hydroxyl groups of the polyenic substance, thus preventing the formation of certain by-products.

In the preparation of the esters of N-substituted partricins, it is obvious that the direct procedure of esterification of the N-derivative of partricin can be substituted by the alternative procedure of first esterifying the carboxyl group of partricin and then subsequently introducing the N-substituent. The latter procedure must, of course, be used when the N-radical contains a carboxyl or other group which is reactive with diazo compounds and when it is desired to prevent such a reaction, which would give, for example, a polyesterified compound.

The synthesis described above using diazo compounds is not, of course, the only one possible; other methods of esterification can also be employed. However, the high intraperitoneal toxicity of the polyenes in general and also of partricin, make it desirable to limit or, if possible, completely avoid the presence of even traces of unreacted material, i.e. to use for the esterification, highly reactive substances which ensure that the reaction proceeds quantitatively. In these circumstances, the use of the diazo compounds is obviously advantageous, compared to other reagents. The use of appropriate purification procedures is, however, a further guarantee of the absence of unreacted starting material.

The preparation of the N-derivatives of partricin or of the esters of partricin presents no difficulties but the reaction time and temperature have to be carefully chosen because of the characteristics of the reagent used for the reaction. If the reaction conditions are too mild, then instead of giving completely substituted derivatives, the N-substituent might only be introduced totally or partially on one of the two nitrogen-containing groups of partricin.

Broadly speaking, the N-derivatives of partricin include the N-acylation and N-alkylation products, the acyl or alkyl radicals of which preferably contain up to 6 carbon atoms. In the case of the N-acylation products, these can be derived from appropriate mono-, di- or polycarboxylic acids.

Generally, an excess of an appropriate reagent, for example an acid anhydride, is added to a diluted suspension of the polyenic substance, preferably in an alcohol of low molecular weight, such as methanol, or in an appropriate solvent, such as dimethylsulphoxide or dimethylacetamide, and in the presence of methanol, as diluent.

As the polyenes are polyhydroxy compounds, this solvent is able to protect the hydroxyls from attack by the reagent used in excess. The reaction mixture is stirred for a few hours, for example from 0.5 to 15 hours, at temperatures varying from 0° to 40°-60°C. but generally at about ambient temperature. As the reaction proceeds, material in suspension gradually passes into solution; in some cases, when the reaction mixture is left to stand, a subsequent precipitation of the derivative formed may occur: otherwise, the solution is filtered to remove any unreacted material and the product is precipitated with appropriate solvents, for example diethyl ether, petroleum ether or the like. After purification with appropriate mixtures of solvents or by column chromatography on silica gel, the N-derivatives of partricin or its esters can be obtained in good yields and in a high state of purity.

The analysis of the new esters of the present invention, and of the N-derivatives of partricin which may be used as intermediates, can be carried out by numerous techniques: the ultra-violet spectrum, which remains substantially unchanged as compared to the starting materials in the frequency of the absorption maxima (average around 400, 380, 360, 340 m$\mu$ in ethanolic solution) shows that the heptaenic structure has remained unchanged; the slight diminution of the intensity of absorption is due to the increase in the molecular weight of the new derivatives. The structure of the esters is confirmed by the disappearance of the acidity of partricin (insolubility in alkali) and by the infra-red spectra, which show a strong absorption band due to the stretching of an ester C=O at frequencies above 1710–1720 cm$^{-1}$. The analysis on silica gel $F_{254}$ is also of great importance in revealing, under ultraviolet light, the gradual formation of the various derivatives and the total disappearance of the reagent: as an overall result, it can be observed that, in a solvent system such as butanol-ethanol-acetone-concentrated aqueous ammonium hydroxide solution (2:5:1:3), alkyl esterification and also the N-acylation give derivatives with high Rf values; however, the presence of particular substituents in the alkyl or acyl radical, for example a carboxyl group, have the opposite action and can, therefore, lead to derivatives with lower Rf values. It is interesting to observe that the new esters of partricin give, with thin layer chromatography, only one spot of microbiologically active substance. It is known, however, that the polyenic antibiotics, upon more detailed analytical investigation, are often shown to consist of two or more substances of similar biological structure and activity. If a similar situation existed in the case of partricin, the esters derived therefrom would obviously also contain an equal number of components.

The microbiological activity spectrum of the new esters is similar to that of the starting materials, i.e. partricin and its N-derivatives: they are almost inactive against bacteria but are very active against numerous fungi and protozoa. Thus, for example, the short-chain alkyl esters of partricin have a minimum inhibitory concentration on numerous strains of Candida albicans of 0.1–0.3 mcg./ml., i.e. they are just as or more active than the starting partricin; they also show an MIC value against certain strains of Trichomonas vaginalis of about 1 mcg./ml. and thus have an activity which, albeit slightly lower than that of the parent compound, is nonetheless of great use from a practical standpoint. The variation in the degree of activity against Candida and Trichomonas, in passing from the polyenic antibiotic to its esters, can rightly be considered to be of great theoretical and practical interest which has hitherto not been matched by any compounds known from the literature.

In addition to the above-mentioned microbiological properties, the new esters of partricin have a strongly reduced toxicity when compared to the parent antibiotic: their acute toxicity ($LD_{50}$) in mice is generally over 2000 mg./kg. by the oral route and about 200 mg./kg. after administration in suspension by the peritoneal route. The haemolytic action is also considerably reduced.

The alkyl esters of partricin N-derivatives often behave in a similar way, substantially maintaining the potency of microbiological activity of the starting substances but showing a reduced toxicity; however, the compounds to be esterified, i.e. N-substituted partricins, are generally less active than the parent substance, inhibiting the growth of Candida albicans at concentrations of about 1–10 mcg./ml. and the growth of Trichomonas vaginalis at concentrations which are not much lower. Furthermore, they still have a rather high toxicity (LD$_{50}$ around 1–20 mg./kg., suspension i.p. mice).

It can be concluded, therefore, that although the results concerning the above-mentioned new esters of N-substituted partricin cannot be easily summarised as a whole, because they present considerable variations from one derivative to another, they generally have MIC values against numerous strains of *Candida albicans* and *Trichomonas vaginalis* of 1–10 mcg./ml.; furthermore, their LD$_{50}$ values, after peritoneal administration in suspension to mice, is always well above 20 mg./kg., reaching, at times, values which are ten to twenty times higher or even more.

The microbiological and toxicological properties mentioned above clearly show that the esters of partricin and of the N-derivatives of partricin are a particularly interesting class of substances which are similar to or better than the known polyenic antibiotics used therapeutically. They are of practical use for combating many fungal and protozoal infections in human and veterinary medicine. They can also be used as pesticides for plants by spraying the new compounds, after mixing with appropriate diluents or by mixing them with fertilisers.

In human medicine, dermatological use against *Candida albicans* and *Trichomonas vaginalis* is particularly important and the substance can be advantageously used in the form of an ointment, tincture, lotion, cream, spray foam or the like or as vaginal tablets or suppositories in effervescent or non-effervescent forms.

Because the insoluble derivatives are only sparingly absorbed in the intestinal tract, they can be administered orally for combating many mycotic intestinal infections, especially those which appear after the prolonged use of antibacterial antibiotics.

Administration can be in the form of tablets, capsules, granules and similar pharmaceutical forms adapted for oral use.

In addition, the possibility of having compounds which are water-soluble or, at least, can be mixed with a large variety of non-toxic organic solvents or with surfactants, does not exclude the possibility of absorption and use for combating generalised infections, whether administered by the oral or parenteral route. For all the uses, the new compounds are admixed with an appropriate amount of solid or liquid pharmaceutical diluent or carrier.

The following Examples are given for the purpose of illustrating the present invention:

EXAMPLE 1

5 g. Finely-powdered partricin are suspended in 200 ml. methanol and the mixture is cooled with ice water. While stirring, 30 g. acetic anhydride are slowly added dropwise, the mixture being kept at ambient temperature for 1 hour. The material initially present in suspension passes gradually into solution and, finally, a small amount of undissolved material is filtered off. Excess diethyl ether is then added, to give a dark yellow, crystalline precipitate of N,N'-diacetyl-partricin. The yield is practically theoretical. The substance can then be advantageously purified, if desired, by appropriate mixtures of methanol and ether and then dried and analysed by the usual chemical and biological methods. The ultraviolet spectrum (ethanolic solution) and the infra-red spectrum (nujol mull) is given in FIGS. 1 and 2 of the accompanying drawings. Thin layer chromatographic analysis, carried out on silica gel F$_{254}$ plates with an eluent system containing butanol-ethanol-acetone-concentrated aqueous ammonium hydroxide solution (2:5:1:3), demonstrates the substantial purity of the product and gives an Rf value of about 0.65 which differs from that of the partricin used as starting material.

N,N'-diacetyl-partricin inhibits the growth of a strain of *Candida albicans* (MIC) at the dilution of 5–10 mcg./ml. and also inhibits the growth of a strain of Trichomonas vaginalis at 1–2 mcg./ml.; its acute toxicity (LD$_{50}$), after administration in suspension to mice by the peritoneal route, is about 3 mg./kg.

EXAMPLE 2

5 g. Partricin are dissolved in 75 ml. dimethylsulphoxide and the solution is filtered and diluted with 75 ml. methanol. The mixture is cooled with ice water and then 5 g. acetic anhydride are added dropwise, with slow stirring, whereafter the mixture is kept at ambient temperature for 1 hour, filtered and the product precipitated with excess ether. After isolation by filtration, the precipitate is washed thoroughly with water to remove any residual solvent. It is then dried in a vacuum to give a high yield of N,N'-diacetyl partricin.

When repeating the process of this Example but reacting the partricin for a longer time with the appropriate fatty acid anhydrides, there are obtained, for example, N,N'-dipropionyl-partricin (thin layer chromatography = Rf about 0.67) and N,N'-dibutyryl-partricin (Rf around 0.68).

EXAMPLE 3

3 g. Partricin are suspended in 150 ml. methanol, the mixture is cooled to 0°C. and then 15 g. succinic anhydride are added. The mixture is stirred for 2 hours at a temperature of up to 35°–40°C., whereafter the large amount of suspended solid material is filtered off. The methanolic solution thus obtained is treated with an excess of a 1:1 mixture of diethyl ether-petroleum ether to precipitate out the reaction product. The isolated product is repeatedly triturated with large amounts of chloroform to remove unreacted succinic anhydride, a high yield of crude N,N'-disuccinyl-partricin being obtained. The product is treated with 80 ml. ethanol, stirred, while cooling, for 2 hours and then any solid in suspension is filtered off and the methanolic solution precipitated with excess diethyl ether. N,N'-disuccinyl-partricin is thus obtained as a relatively pure, yellow, crystalline solid. Thin layer chromatography on silica gel, with the above-mentioned eluent, gives an Rf value of about 0.45. The minimum inhibitory concentration of the product is about 5 mcg./ml. against *Candida albicans* and about 1 mcg./ml. against *Trichomonas vaginalis;* the LD$_{50}$, determined with a suspension, is about 2 mg./kg. (by intraperitoneal route in mice).

EXAMPLE 4

Reaction of partricin with various anhydrides of dicarboxylic acids, for example, with maleic anhydride, in a manner analogous to that used in the previous Examples, gives the corresponding N-substituted derivatives, for example, N-maleoyl derivative. The Rf value on thin layer chromatography is about 0.45. The MIC value is 10–20 mcg./ml. against *Candida albicans* and 2–4 mcg./ml. against *Trichomonas vaginalis*. The toxicity of the compound (LD$_{50}$), determined after peritoneal administration in suspension, in mice is about 6 mg./kg.

EXAMPLE 5

Figure 3:
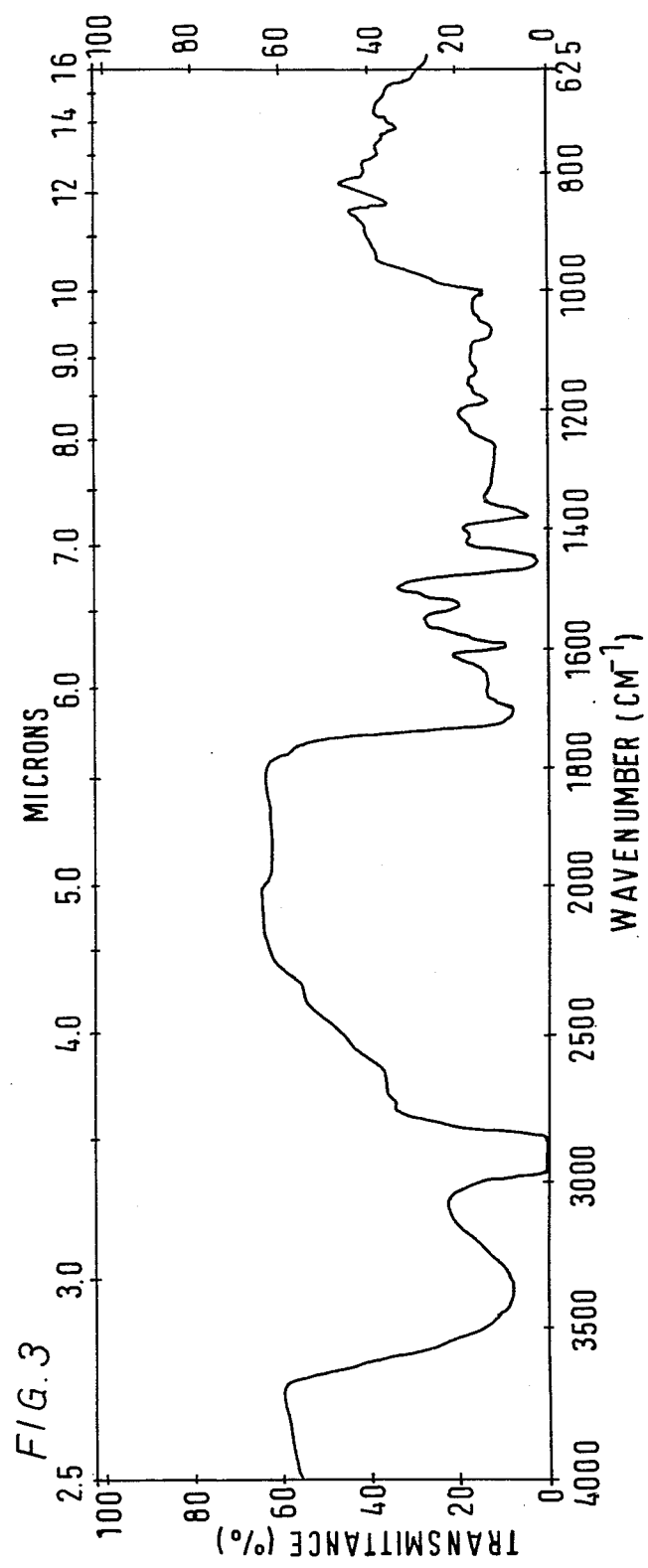

In accordance with the procedure of the previous Examples, partricin is reacted with phthalic anhydride (or with other anhydrides of aromatic dicarboxylic acids) to give high yields of the N-phthalyl derivative. It can easily be analysed by infra-red spectrum (nujol mull, see FIG. 3 of the accompanying drawings) and by other routine analytical techniques. The compound inhibits the growth of Candida albicans at a concentration of about 5 mcg./ml. and inhibits the growth of Trichomonas vaginalis at a concentration of 1–2 mcg./ml., while the $LD_{50}$ value is about 8 mg./kg. (i.p. suspension mice).

EXAMPLE 6

Figure 4:
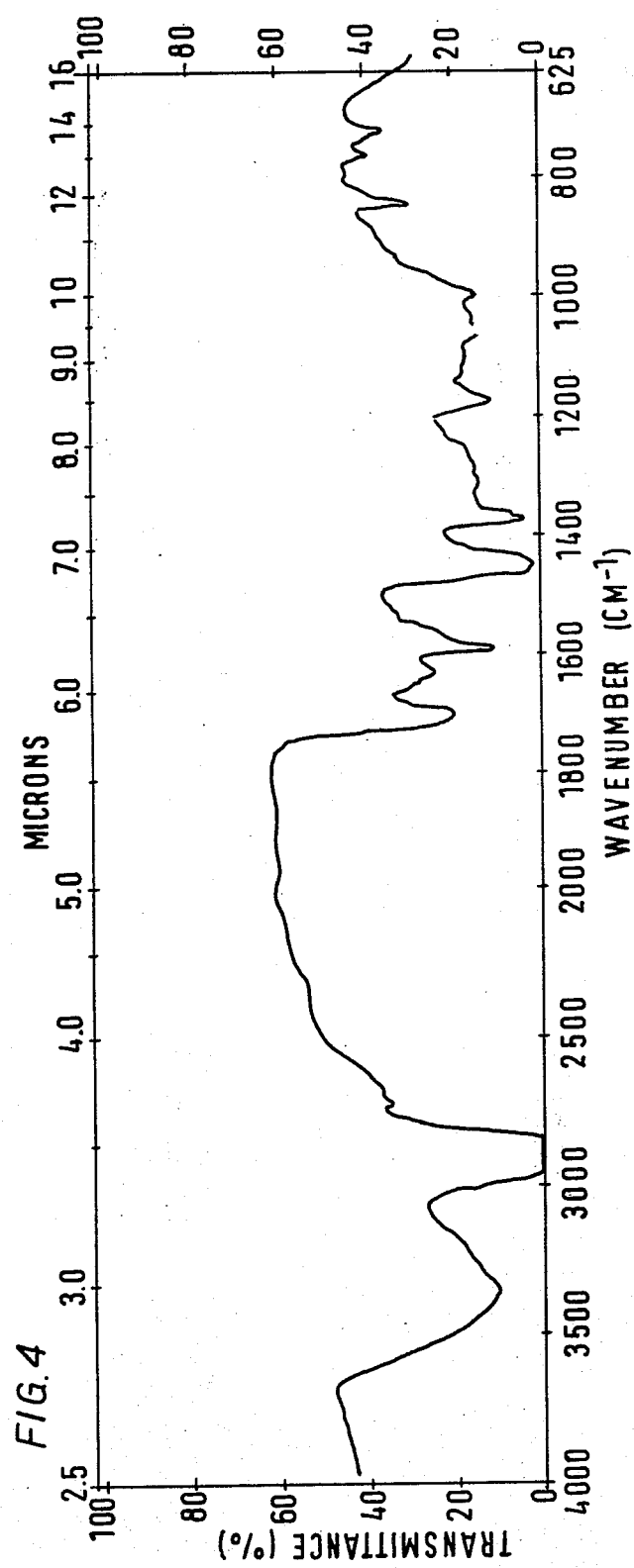

10 g. Partricin are dissolved in 100 ml. dimethylsulphoxide and then 100 ml. ethereal diazoethane solution are cautiously added, while stirring slowly and cooling with ice water. Great care is taken during the process because of the potentially dangerous nature of the reagent. At the end of the reaction, i.e. when the evolution of nitrogen has finished, the mixture is brought to ambient temperature and left to stand for 6 hours, stirring occasionally. At the end of this time, the solution is filtered to remove any traces of solid in suspension and excess diethyl ether is added to precipitate the product. The solid obtained is filtered off and washed thoroughly first with ether and then with water. It is then dried in a vacuum oven at ambient temperature to give a high yield of partricin ethyl ester in the form of a yellow crystalline solid. If required, the product can be further purified from dimethylsulphoxide-acetone-ether, dimethylacetamide-water or the like or by chromatography on a silica gel column. The ultraviolet spectrum of the compound is similar to that of the above-described derivatives (cf. FIG. 1 of the accompanying drawings), having absorption maxima at 401, 378, 359 and 340 m$\mu$ in ethanolic solution; the infra-red spectrum (nujol mull) of the product is shown in FIG. 4 of the accompanying drawings. Thin layer chromatography on silica gel $F_{254}$, with butanol-ethanol-acetone-concentrated aqueous ammonium hydroxide solution (2:5:1:3) as eluent, gives an Rf value of about 0.85. The biological analysis of partricin ethyl ester shows a minimum inhibitory concentration of about 0.3 mcg./ml. against numerous strains of Candida albicans and of about 2 mcg./ml. against Trichomonas vaginalis; the toxicity ($LD_{50}$), in suspension, in mice is about 100 mg./kg. by the peritoneal route and over 2000 mg./kg. by the oral route.

EXAMPLE 7

To a solution of 25 g. partricin in 250 ml. dimethylsulphoxide, are added, while stirring, about 2 ml. concentrated aqueous ammonium hydroxide solution, i.e. enough to adjust the pH of the solution to about 10, the pH being measured after dilution of a sample to 1% by adding a 1:1 mixture of dimethylsulphoxide and water. It is then cooled with ice water and 250 ml. ethereal diazoethane solution are added, proceeding as in Example 6. After the final isolation, the partricin ethyl ester thus prepared appears to be similar to the ester obtained in the previous Example with regard to its physico-chemical properties, having the same chromatographic Rf values and similar ultra-violet and infra-red spectra; however, it has lower MIC values against Candida albicans (about 0.15 mcg./ml.) and against Trichomonas vaginalis (about 1 mcg./ml.) and has, therefore a major microbiological activity.

EXAMPLE 8

A solution of partricin in dimethylsulphoxide or in dimethylacetamide is treated with an excess of an ethereal solution of diazo-n-propane in the presence of ammonium hydroxide, following the procedure described in Example 7. The partricin n-propyl ester thus obtained has an Rf of about 0.88 in thin layer chromatography on silica gel $F_{254}$, carried out under the conditions described above. The minimum inhibitory concentrations are about 0.3 mcg./ml. against Candida albicans and about 1 mcg./ml. against Trichomonas vaginalis.

EXAMPLE 9

Proceeding as described in Example 7 but reacting the partricin with diazo-n-butane, gives the corresponding n-butyl ester. The chromatographic analysis gives an Rf value of about 0.90 (thin layer chromatography); the MIC is about 0.3 mcg./ml. against Candida albicans and 1–2 mcg./ml. against Trichomonas vaginalis, while the $LD_{50}$ is over 2000 mg./kg. after oral administration.

EXAMPLE 10

To a solution of 5 g. N,N'-diacetyl-partricin in 50 ml. dimethylsulphoxide are added 50 ml. ethereal diazomethane solution, in the manner described in Example 6. After standing for 6 hours at ambient temperature, the product is precipitated out with excess ether, filtered off, washed thoroughly with ether and water and then dried at ambient temperature in a vacuum. A high yield of N,N'-diacetyl-partricin methyl ester is obtained in the form of a yellow, crystalline solid which can be purified from appropriate solvent mixtures. Chromatography on silica gel $F_{254}$ plates, using butanol-ethanolacetone-concentrated ammonium hydroxide solution (2:5:1:3) as eluent, gives an Rf value of about 0.86. The ultraviolet spectrum shows the characteristic behaviour of the heptaenic substances already described above for other derivatives (cf. FIG. 1 of the accompanying drawings). N,N'-diacetyl-partricin methyl ester inhibits the growth of Candida albicans and Trichomonas vaginalis at about the same concentrations (5–10 mcg./ml.) and is only moderately toxic to mice by the oral and peritoneal routes.

EXAMPLE 11

Reaction of appropriate N-derivatives of partricin with appropriate diazo compounds according to the methods described in Examples 6 and 7 gives the following esters:
N,N'-diacetyl-partricin n-propyl ester,
N,N'-diacetyl-partricin n-butyl ester,
N,N'-dipropionyl-partricin ethyl ester, and
N,N'-dibutyryl-partricin methyl ester.

EXAMPLE 12

Reaction of N,N'-disuccinyl-partricin with excess diazomethane according to the process described in Example 6 gives a substantially quantitative yield of N,N'-disuccinyl-partricin trimethyl ester. Thin layer chromatographic analysis gives a spot with an Rf value of about 0.90, demonstrating the substantial purity of the product. It has a marked microbiological activity and is equally potent against Candida and Trichomonas.

EXAMPLE 13

Reaction of appropriate N-derivatives of partricin with appropriate diazo compounds gives the following analogues of the compound of Example 12:
N,N'-disuccinyl-partricin triethyl ester, and
N,N'-disuccinyl-partricin tri-n-propyl ester.

EXAMPLE 14

5 g. Partricin methyl ester in 200 ml. methanol are treated, while cooling, with 30 g. acetic anhydride, whereafter the mixture is left to stand for 2 hours at ambient temperature, with gentle agitation (see Example 1). Subsequent precipitation with excess diethyl ether and purification with a conventional solvent mixture gives a high yield of the desired N,N'-diacetyl-partricin methyl ester. This product is identical with that obtained by the different process described in Example 10, having the same physico-chemical or microbiological properties.

Similar procedures can be used to produce analogous compounds of Example 11.

EXAMPLE 15

3 g. Partricin methyl ester in 150 ml. methanol are treated, while cooling, with 15 g. succinic anhydride. After standing for at least 2 hours at a temperature between ambient temperature and 40°C., the product is precipitated with excess diethyl ether and purified as described in Example 3. N,N'-disuccinyl-partricin methyl ester is thus obtained and has a Rf of about 0.73 in thin layer chromatography. It inhibits the growth of *Candida albicans* and *Trichomonas vaginalis* at the dilution of about 5 mcg./ml.; the $LD_{50}$ in mice, by the oral route, is over 2000 mg./kg.

Analogous procedures give the following derivatives:
N,N'-disuccinyl-partricin ethyl ester, and
N,N'-disuccinyl-partricin n-propyl ester, The present invention also provides pharmaceutical compositions, which can be administered orally or parenterally, containing at least one of the new alkyl esters, in admixture with a solid or liquid pharmaceutical carrier.

Solid compositions for oral, rectal or vaginal administration include compressed tablets, effervescent tablets, pills, dispersable powders, capsules, granules and suppositories. In such solid compositions, the active material is admixed with at least one inert diluent, such as calcium carbonate, starch, alginic acid or lactose. The compositions may also comprise, as is normal practice, additional substances other than inert diluents, for example, lubricating agents, such as magnesium stearate.

Liquid compositions for oral administration include pharmaceutically acceptable emulsions, solutions, suspensions, syrups and elixirs containing inert diluents commonly used in the art, such as water and liquid paraffin. Besides inert diluents, such compositions may also comprise adjuvants, such as wetting and suspension agents and sweetening and flavoring agents.

The compositions according to the present invention, for oral administration, include capsules of absorbable material, such as gelatine, containing the active material, with or without the addition of diluents or excipients.

Preparations according to the present invention for parenteral administration include sterile aqueous or nonaqueous solutions, suspensions or emulsions. Examples of non-aqueous solvents or suspending media include propylene glycol, polyethylene glycol, vegetable oils, such as olive oil, and injectable organic esters, such as ethyl oleate. These compositions may also contain adjuvants, such as wetting, emulsifying and dispersing agents. They may be sterilised, for example, by filtration through bacteriaretaining filters, by incorporation into the compositions of sterilising agents, by irradiation or by heating. They may also be produced in the form of sterile solid compositions, which can be dissolved in sterile water or some other sterile injectable medium immediately before use.

The percentage of active ingredient in the compositions of the present invention may be varied, it being necessary that it should constitute a proportion such that a suitable dosage for the desired therapeutic effect shall be obtained.

Examples of pharmaceutical compositions containing the polyene antibiotic include the following:

Example 16

Ointment
Composition:
| | | |
|---|---|---|
| partricin ethyl ester | 0.5 | g. |
| alcoholic fats | 60 | g. |
| lanolin | 15 | g. |
| polyethylene glycol 1540 monostearate | ad 100 | g. |

Example 17

Liniment
Composition:
| | | |
|---|---|---|
| N,N'-diacetyl-partricin methyl ester | 0.5 | g. |
| dimethylacetamide | 5 | g. |
| anhydrous lanolin | 15 | g. |
| cetyl alcohol | 30 | g. |
| oleyl alcohol | 15 | g. |
| sorbitan trioleate | 10 | g. |
| polyethylene glycol 1540 monostearate | 24 | g. |

Example 18

Vaginal suppositories
Each vaginal suppository contains:
| | | |
|---|---|---|
| N,N'-disuccinyl-partricin methyl ester | 5 | mg. |
| dimethyl acetamide | 50 | mg. |
| polyethylene glycol 1540 monostearate | 1.35 | g. |
| cetyl alcohol | 0.500 | g. |

Example 19

Vaginal suppositories
Each vaginal suppository contains:
| | | |
|---|---|---|
| N,N'-disuccinyl-partricin tripropyl ester | 25 | mg. |
| dimethyl acetamide | 50 | mg. |
| polyethylene glycol 1540 monostearate | 1.35 | g. |
| cetyl alcohol | 0.500 | g. |

The pharmaceutical compositions illustrated in Examples 16 to 19 above show valuable anti-fungal and anti-protozoal activity when administered to humans.

We claim:

1. The $C_{1-6}$ alkyl esters of N-substituted partricin wherein the N-substituents are $C_{1-6}$ alkyl or $C_{1-6}$ carboxylic acyl.

2. The $C_{1-6}$ alkyl esters of claim 1 produced by reaction of the N-substituted partricin with the corresponding diazoalkane.

Figure 2:
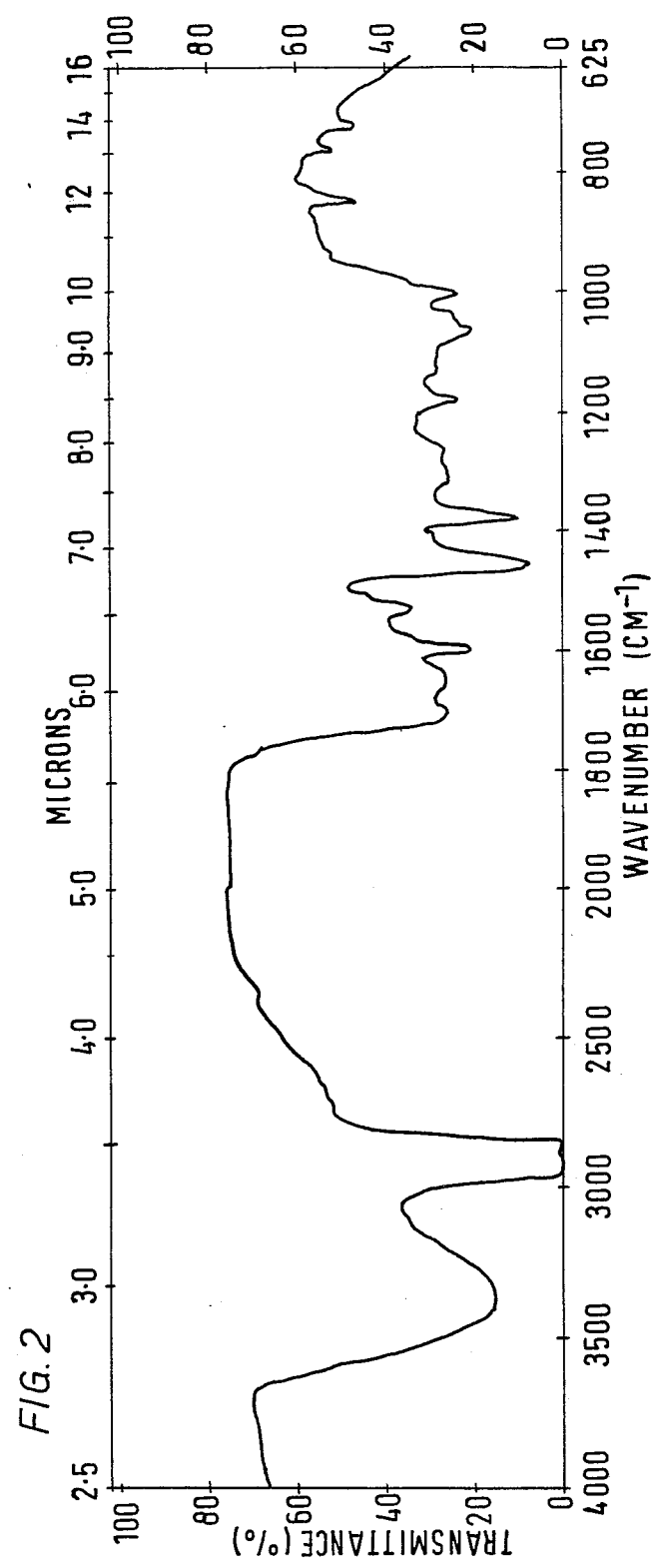

3. N,N'-Diacetyl-partricin methyl ester according to claim 1, having a Rf value of 0.86 using a butanol, ethanol, acetone, concentrated ammonium hydroxide eluent (2:5:1:3) on silica gel $F_{254}$ plates and having the ultraviolet spectrum substantially as depicted in FIG. 1 and inhibition of growth of *Candida albicans* and *Trichomonas vaginalis* at 5–10 mcg./ml.

* * * * *